United States Patent
Dejima

(10) Patent No.: US 8,523,358 B2
(45) Date of Patent: Sep. 3, 2013

(54) INFORMATION PROCESSING APPARATUS, METHOD, AND STORAGE MEDIUM STORING PROGRAM

(75) Inventor: Tatsuya Dejima, Tokyo (JP)

(73) Assignee: Casio Computer Co., Ltd., Tokyo (JP)

(*) Notice: Subject to any disclaimer, the term of this patent is extended or adjusted under 35 U.S.C. 154(b) by 0 days.

(21) Appl. No.: 13/336,235

(22) Filed: Dec. 23, 2011

(65) Prior Publication Data

US 2012/0162603 A1 Jun. 28, 2012

(30) Foreign Application Priority Data

Dec. 27, 2010 (JP) ................................ 2010-290417

(51) Int. Cl.
*A61B 3/14* (2006.01)

(52) U.S. Cl.
USPC .............................. 351/210; 345/158; 396/51

(58) Field of Classification Search
USPC ................. 345/156–158; 351/209, 210, 246; 382/117; 396/51; 715/856–862, 865
See application file for complete search history.

(56) References Cited

U.S. PATENT DOCUMENTS

| | | | | |
|---|---|---|---|---|
| 4,836,670 A | * | 6/1989 | Hutchinson | 351/210 |
| 5,471,542 A | * | 11/1995 | Ragland | 382/128 |
| 5,731,805 A | * | 3/1998 | Tognazzini et al. | 345/156 |
| 5,912,721 A | * | 6/1999 | Yamaguchi et al. | 351/210 |
| 6,106,119 A | * | 8/2000 | Edwards | 351/209 |
| 6,231,185 B1 | * | 5/2001 | Pipa | 351/208 |
| 6,351,273 B1 | * | 2/2002 | Lemelson et al. | 715/786 |
| 2005/0047629 A1 | * | 3/2005 | Farrell et al. | 382/117 |
| 2006/0209013 A1 | * | 9/2006 | Fengels | 345/156 |

FOREIGN PATENT DOCUMENTS

| | | |
|---|---|---|
| JP | 6-289985 A | 10/1994 |
| JP | 06-347866 A | 12/1994 |
| JP | 8-238222 A | 9/1996 |
| JP | 09-018760 A | 1/1997 |
| JP | 2001-061785 A | 3/2001 |
| JP | 2006-323769 A | 11/2006 |
| JP | 2007-029126 A | 2/2007 |

(Continued)

OTHER PUBLICATIONS

Y. Sawahata et al; A Gaze Measurement System Permitting a Head Motion; FIT2004; (The 3$^{rd}$ Forum on Information Technology) p. 563-564; Sep. 8, 2004.

(Continued)

*Primary Examiner* — Darryl J Collins
*Assistant Examiner* — Gary O'Neill
(74) *Attorney, Agent, or Firm* — Holtz, Holtz, Goodman & Chick, PC

(57) ABSTRACT

A display unit 11 has a display area of a predetermined shape and displays an image on the display area. An image capturing unit 12 generates data of a captured image by capturing an image of an eye 2 of a user in which the display area is reflected. A reference detection unit 21 detects a moving reference point that moves along with the movement of user's eye-gaze and an unmoving reference point that can be assumed as approximately stationary regardless of the user's eye-gaze movement, and generates a vector drawn from the unmoving reference point to the moving reference point as a shift amount $V(x,y)$. An eye-gaze detection unit 22 detects a movement vector $\Delta V(\Delta x, \Delta y)$ as the user's eye-gaze movement amount based on a reference shift amount $V_o(x_o, y_o)$ generated in the past and the shift amount $V(x,y)$ currently generated.

6 Claims, 11 Drawing Sheets

(56) References Cited

FOREIGN PATENT DOCUMENTS

| | | |
|---|---|---|
| JP | 2007-066274 A | 3/2007 |
| JP | 2007-072861 A | 3/2007 |
| JP | 2007-271773 A | 10/2007 |
| JP | 2010-233896 A | 10/2010 |

OTHER PUBLICATIONS

Japanese Office Action dated Jan. 29, 2013 (and English translation thereof) in counterpart Japanese Application No. 2010-290417.

* cited by examiner

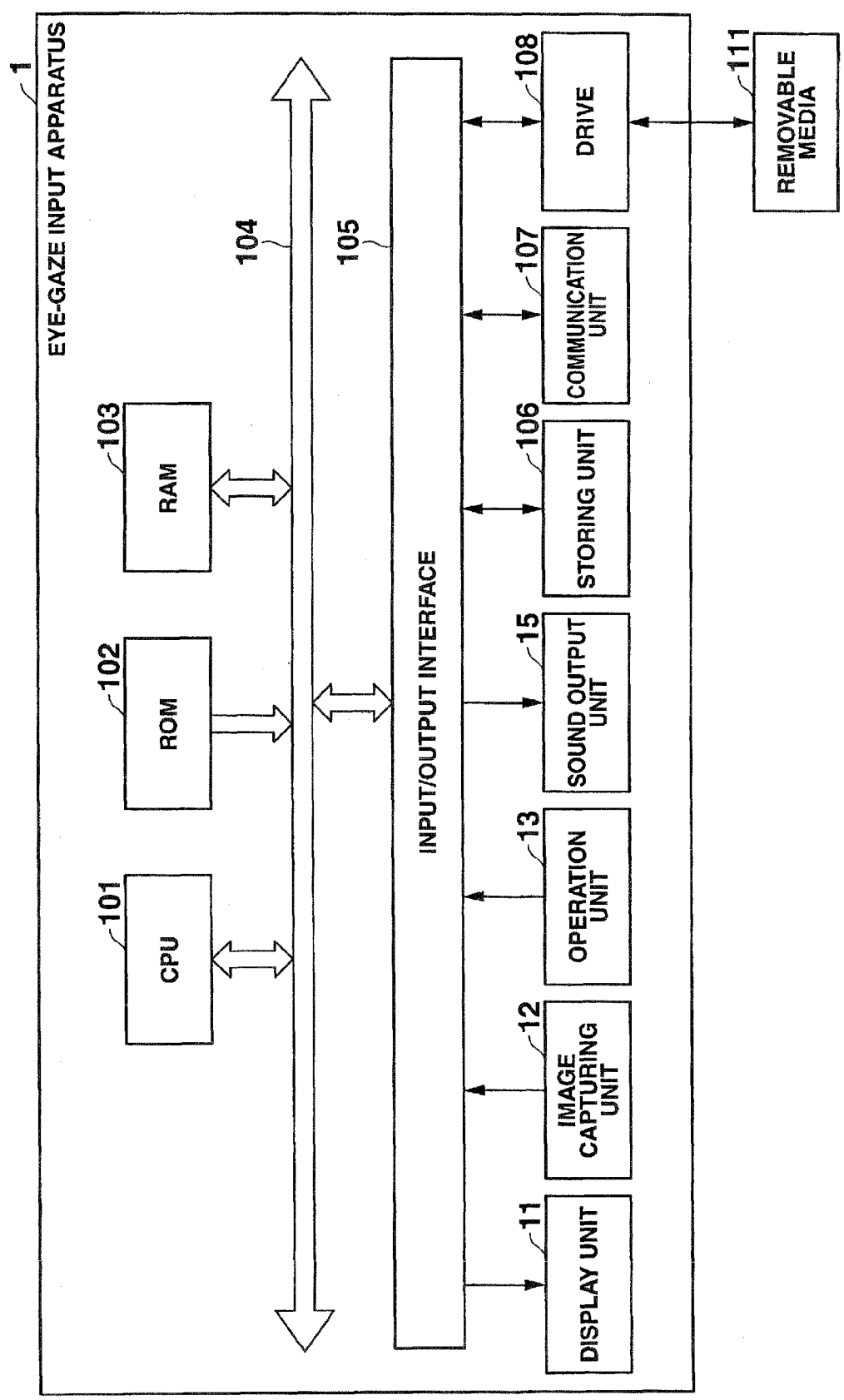

INFORMATION PROCESSING APPARATUS, METHOD, AND STORAGE MEDIUM STORING PROGRAM

This application is based upon and claims the benefit of priority from the prior Japanese Patent Application No. 2010-290417, filed on Dec. 27, 2010, the entire contents of which are incorporated herein by reference.

BACKGROUND OF THE INVENTION

1. Field of the Invention

The present invention relates to an information processing apparatus, method, and storage medium having stored therein a program, more particularly to a technology that enables a user to realize an operation equivalent to a mouse operation simply by moving the eye in a state in which the head is not being constrained.

2. Related Art

Conventionally, as an operation of inputting information to an information processing apparatus such as a personal computer, an input operation using an input device is employed. Especially, an input operation using a mouse, i.e., a so-called mouse operation is widely employed as the input operation using an input device. As an exemplary mouse operation, there is known an operation of moving a mouse pointer to an icon or the like, and clicking the icon or the like to select it.

Recently, there is a demand for allowing a user watching a screen including a mouse pointer to realize an input operation (hereinafter, referred to as a "mouse equivalent operation") equivalent to the mouse operation, by simply moving his or her eye, without using a mouse. In order to meet such a demand, for example, technologies for detecting a position of a line of sight (hereinafter, referred to as "gaze position") of a human eye are developed and disclosed in Japanese Patent Application Publication No. 1997-18760, Japanese Patent Application Publication No. 2001-61785, and Japanese Patent Application Publication No. 1994-347866.

However, in the technologies disclosed by the aforementioned publications, it is premised that the user's head is constrained in some way, such that the user looks into a finder while his head is fixed, or the user wears a head mount display on the head.

Since it is unpleasant for a user to have his or her head constrained only for the purpose of the mouse equivalent operation, it is desired to realize the mouse equivalent operation without having the head of the user constrained.

The present invention is conceived in view of the above-described circumstances, and it is an object of the present invention to enable a user to realize the mouse equivalent operation simply by moving the eye in a state in which the head is not being constrained.

SUMMARY OF THE INVENTION

In accordance with one aspect of the present invention, there is provided an information processing apparatus, comprising:
  a first image detection unit that detects, as a first image, an image indicative of a specific part of an eye in captured image data supplied from an image capturing unit connected therewith;
  a first detection unit that identifies a position of the first image in the captured image data;
  a second image detection unit that detects, as a second image, an image indicative of an object of a specific shape reflected by the eye from the captured image data;
  a second detection unit that identifies a position of the second image in the captured image data; and
  an eye-gaze movement amount detection unit that detects a movement amount of a gaze of the eye captured by the image capturing unit based on a relationship between positions of the first image and the second image.

In accordance with another aspect of the present invention, there is provided an image processing method and a storage medium corresponding to the information processing apparatus described in the above.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 15 is a block diagram showing a hardware configuration of the eye-gaze input apparatus shown in FIG. 6.

DETAILED DESCRIPTION OF THE INVENTION

The following describes an embodiment of the present invention with reference to drawings.

Figure 1:
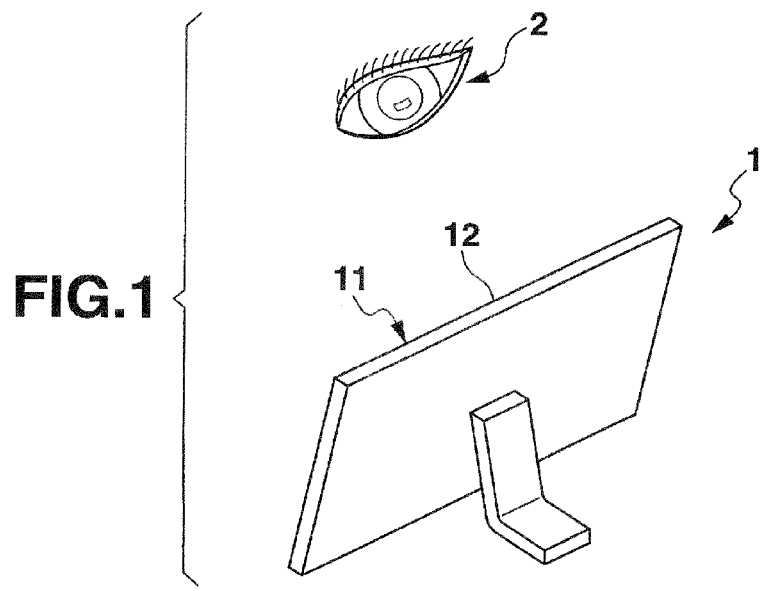
FIG. 1 is a rear perspective view showing an external configuration of an eye-gaze input apparatus as one embodiment of the information processing apparatus according to the present invention.

FIG. 1 is a rear perspective view showing an external configuration of an eye-gaze input apparatus 1 as one embodiment of the information processing apparatus according to the present invention.

As shown in FIG. 1, the eye-gaze input apparatus 1 is configured as a digital photo frame. The front surface (the surface not shown in FIG. 1) of the eye-gaze input apparatus 1 is provided with a display unit 11 and an image capturing unit 12.

The user can perform the mouse equivalent operation simply by moving a line of sight (hereinafter referred to as "gaze") of an eye 2 watching the display unit 11 without having his or her head constrained in any manner.

This means that the eye-gaze input apparatus 1 detects the gaze position of the eye 2 of the user, recognizes a mouse equivalent operation based on the detection result, inputs information (such as an instruction to move the mouse pointer, an instruction to select an item by clicking thereon or the like) by the mouse equivalent operation, and can thereby carry out corresponding processing.

In the following, a specific description will be given of one example of a method employed in the present embodiment of detecting a gaze position of an eye 2 of the user with reference to FIGS. 2 to 5.

Figure 2:
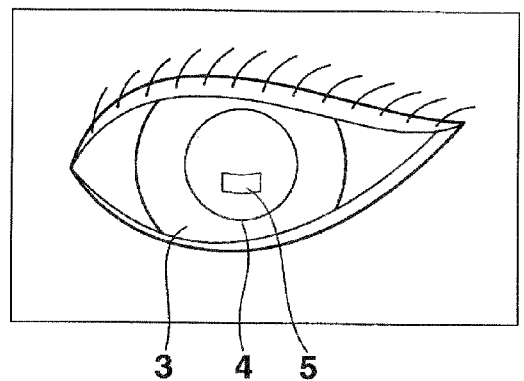
FIG. 2 is a diagram showing a captured image as a result of capturing an image of an eye, which reflects a display unit, illustrating a method of detecting a gaze position by the eye-gaze input apparatus shown in FIG. 1.

FIG. 2 is a diagram showing a captured image as a result of capturing an image of the eye 2, which reflects a display unit 11, illustrating a method of detecting a gaze position by the eye-gaze input apparatus 1.

This means that FIG. 2 shows an example of an image (hereinafter, referred to as a "captured image") acquired as a result that the image capturing unit 12 has captured an image of the eye 2.

The captured image includes an area 3 (hereinafter, referred to as an "eye area 3") of an image of the eye 2. The eye area 3 further includes an area 4 (hereinafter, referred to as a "pupil area 4") of an image of the pupil of the eye 2 and an area 5 (hereinafter, referred to as a "display unit reflection area 5") of an image of a reflection of the display unit 11 in the eye 2.

The eye 2 as the capturing target of the image capturing unit 12 may be either the left eye or the right eye. In the present embodiment, it is assumed that the left eye has been employed as the eye 2 in advance. However, it is to be noted the right eye may be employed as the eye 2 in advance, or either the left eye or the right eye may be selected as the eye 2 afterwards.

Furthermore, the capturing target of the image capturing unit 12 may be both eyes. In this case, the eye-gaze input apparatus 1 can detect various mouse equivalent operations such as operations equivalent to the left and right click operations as combined movements of both eyes, which will be described later.

Here, "eye-gaze detection" of the present embodiment is not intended to mean a detection of an absolute direction of a gaze of the eye 2 but a detection of a relative movement vector (movement amount and movement direction) of a gaze of the eye 2 from a specific point of time in the past to a point of time of detection.

In order to detect the movement vector of a line of sight (hereinafter referred to as "eye-gaze movement vector"), two reference points are identified and used from among a plurality of captured images sequentially captured. The two reference points includes a reference point (hereinafter, referred to as a "moving reference point") that moves along with the eye-gaze, and a reference point (hereinafter, referred to as an "unmoving reference point") to be used as an unmoving origin of a coordinate system of the moving reference point.

Conventionally, a position of a pupil area 4, i.e., a point representative of the pupil area 4 has been employed as the moving reference point, and a position of an eye area 3, i.e., a point representative of the eye area 3 has been employed as the unmoving reference point, in general.

Since the technology of accurately detecting a pupil from data of the captured image is heretofore known, the position of the pupil area 4 can be represented by a pupil center detected by such a technology. On the other hand, it is very difficult to accurately detect the position of the eye area 3 as a whole, unless there is provided a measuring apparatus fixedly positioned with respect to the eye 2. Although feature points such as inner and outer corners of the eye can be detected without such a measuring apparatus, these feature points are not so much clear as the pupil, and therefore, cannot serve to identify an accurate position of the eye area 3.

Accordingly, in order to identify the position of the eye area 3, only the pupil can serve as the most significant feature point. As a result, the pupil is required to be detected. In this case, both positions of the eye area 3 and the pupil area 4 are identified based on the same pupil. Thus, it is virtually impossible to distinguish the positions of the eye area 3 and the pupil area 4.

This means that, unless there is a technology capable of detecting the position of the eye area 3 based on a feature point different from the pupil area 4, it is very difficult to detect the positions of the eye area 3 and the pupil area 4 separately.

For this reason, the conventional technologies such as disclosed by the aforementioned publications need to substantially fix the position of the eye to some degree, and therefore, it is premised that the user's head is constrained in some way.

On the other hand, such constraint of the head is unpleasant and bothersome to the user.

In view of this, in the present embodiment, in order to enable a user to realize the mouse equivalent operation simply by moving the eye in a state in which the head is not being constrained, the following method of eye-gaze detection is employed.

In short, the position of the display unit reflection area 5, which can be detected independently from the position of the pupil area 4, is employed as the unmoving reference point instead of the position of the eye area 3, which has been conventionally in use. In this case, the eye-gaze detection is realized by detecting the relative change of the position of the pupil area 4 as the moving reference point with respect to the position of the display unit reflection area 5 as the unmoving reference point.

Further, in the following, a detailed description will be given of the method of eye-gaze detection of the present embodiment with reference to FIGS. 3 to 5.

Figure 3:
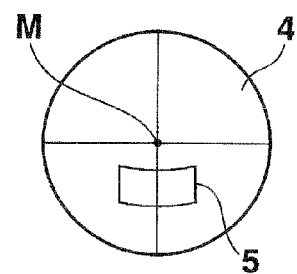
FIG. 3 is an enlarged view of a part of a pupil area 4 in the captured image shown in FIG. 2.

FIG. 3 is an enlarged view of the part of the pupil area 4 in the captured image shown in FIG. 2.

As shown in FIG. 3, in the present embodiment, the pupil center M that represents the position of the pupil area 4 can be identified as the gravity center of the pupil area 4, for example.

Here, in the present embodiment, it is assumed that a gravity center of a predetermined area in the captured image can be acquired as an average of the coordinates of the entire constituent pixels of the predetermined area.

This means that, in the captured image, the horizontal coordinate of the gravity center of the pupil area 4 is calculated as an average of the horizontal coordinates of the entire constituent pixels of the pupil area 4. Similarly, in the captured image, the vertical coordinate of the gravity center of the pupil area 4 is calculated as an average of the vertical coordinates of the entire constituent pixels of the pupil area 4.

The pupil center M thus calculated is employed as the moving reference point of the present embodiment.

Here, in the present embodiment, as the coordinate system of the captured image, such a coordinate system is employed that the pixel at the bottom right corner of the captured image is defined as the origin, and the distance between a pixel and the origin is measured by the numbers of pixels in horizontal and vertical directions.

This means that, in the present embodiment, a leftward axis along the lowermost horizontal side of the captured image is employed as the X-axis, along which the horizontal coordinate is measured. On the other hand, an upward axis along the rightmost vertical side of the captured image is employed as the Y-axis, along which the vertical coordinate is measured.

Such a coordinate system is employed in the present embodiment in consideration of the fact that the eye 2 is positioned in a face-to-face relationship with the display unit 11, and thus, a mirror-image relationship is formed such that, when a gaze of the eye 2 moves from left to right of the display unit 11, the pupil center M moves reversely from right to left in a plurality of sequentially captured images. Also, such a coordinate system is employed for the purpose that, in the eye-gaze detection processing, which will be described later, the direction of the X-axis of the coordinate system of the display unit 11 can be defined rightward in conformity with a general notion.

The method of identifying the pupil center M is not particularly limited to that of the present embodiment, and any method is applicable as long as a point that represents the position of the pupil area 4 can be identified as the pupil center M.

Figure 4:
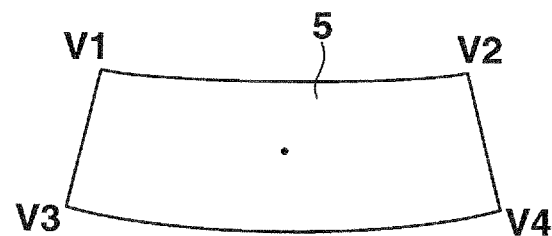
FIG. 4 is an enlarged view of a part of a display unit reflection area 5 in the captured image shown in FIG. 2.

FIG. 4 is an enlarged view of the part of the display unit reflection area 5 in the captured image shown in FIG. 2.

As shown in FIG. 4, since a reflection center Z of the display unit reflection area 5 is positioned approximately at the center of the display unit reflection area 5, the reflection center Z represents the position of the display unit reflection area 5 and therefore is employed as the unmoving reference point of the present embodiment.

For example, the reflection center Z can be identified as follows:

The display unit reflection area 5 is an area acquired as a result of capturing the display unit 11, which is reflected by the eye 2, and is therefore curviform but can be treated approximately as a quasi-rectangle. This means that the display unit reflection area 5 can be treated approximately as a quasi-rectangle having 4 vertices V1 to V4 shown in FIG. 4. By detecting such 4 vertices V1 to V4 from the captured image, the reflection center Z can be easily calculated as the gravity center of the 4 vertices V1 to V4.

This means that, in the captured image, the horizontal coordinate of the reflection center Z is calculated as an average of the horizontal coordinates of the 4 vertices V1 to V4. Similarly, the vertical coordinate of the reflection center Z is calculated as an average of the vertical coordinates of the 4 vertices V1 to V4.

The reflection center Z thus calculated is employed as the unmoving reference point of the present embodiment.

The method of identifying the reflection center Z is not limited to that of the present embodiment, and any method can be employed as long as a point that represents the position of the display unit reflection area 5 can be identified as the reflection center Z.

From the viewpoint of calculating the reflection center Z, it is not necessary to cut out and use the display unit reflection area 5 in a curved form accurately from the captured image. For example, it is also possible to cut out a regular rectangle inscribed in the boundary of the display unit reflection area 5, and calculate the reflection center Z using the regular rectangle. In this way, the display unit reflection area 5 may be cut out in an easily treatable form such as the regular rectangle.

In the following, a description will be given of a method of eye-gaze detection based on a relative relationship in position between the pupil center M (the moving reference point) and the reflection center Z (the unmoving reference point).

As long as the user is gazing at the display unit 11, when the gaze position of the eye 2 of the user moves, the display unit reflection area 5 is approximately stationary in the eye area 3, though the pupil area 4 moves along with the eye-gaze (see FIG. 2).

It should be noted that, when the user moves his or her face, although the eye area 3 as a whole moves in the captured image, the display unit reflection area 5 is approximately stationary in the eye area 3 as long as the user gazes at the display unit 11.

Furthermore, it should be also noted that the position of the display unit reflection area 5 can be easily identified independently from the position of the pupil area 4, while the position of the eye area 3 can be hardly identified independently from the position of the pupil area 4, as described above.

Taking these notable facts into account, the eye-gaze detection can be easily made possible by employing the reflection center Z of the display unit reflection area 5, which is approximately stationary in relation to the eye area 3, as the unmoving reference point, in place of the position of the eye area 3, and introducing a shift amount, which indicates a relative relationship in position between the pupil center M (the moving reference point) and the reflection center Z (the unmoving reference point).

Figure 5:
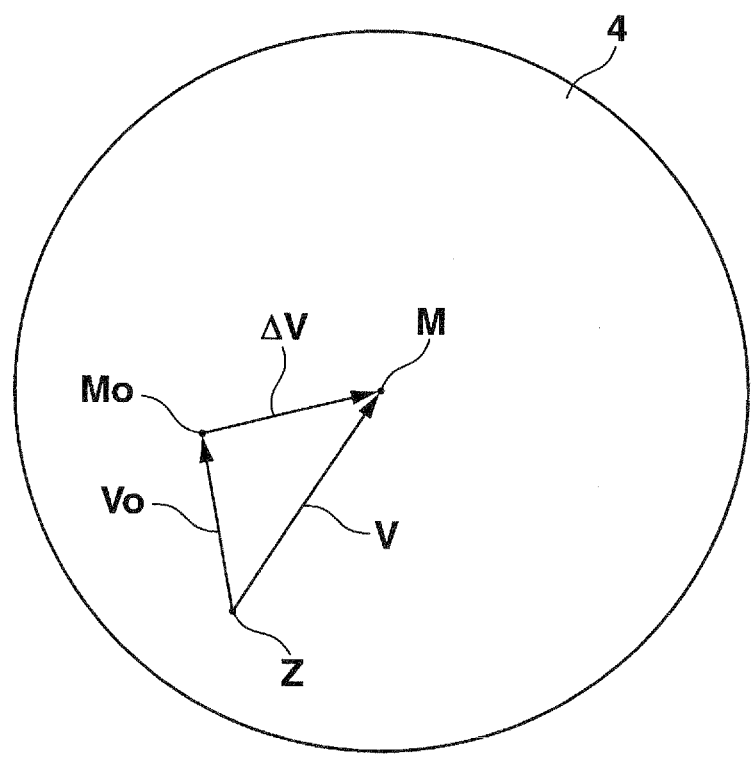
FIG. 5 is an enlarged view of the part of the pupil area 4 in the captured image shown in FIG. 2 illustrating a shift amount that indicates a relative relationship in position between a pupil center and a reflection center.

FIG. 5 is an enlarged view of the part of the pupil area 4 in the captured image shown in FIG. 2 illustrating the shift amount that indicates a relative relationship in position between the pupil center M and the reflection center Z.

As shown in FIG. 5, if the shift amount is defined as a vector $V(x,y)$ from the reflection center Z to the pupil center M, it can be considered that the variation of the shift amount is proportional to the variation of the gaze position of the eye 2 of the user. Therefore, the eye-gaze detection can be easily made possible by detecting the variation of this shift amount.

Here, in order to detect the variation of the shift amount, a shift amount (hereinafter, referred to as a "reference shift amount"), on the basis of which the variation of the shift amount is determined, is required. Therefore, in the present embodiment, calibration is performed for initial setting of the reference shift amount.

The calibration is performed in such a manner that the user performs a predetermined operation with respect to the eye-gaze input apparatus 1 while gazing at the center position of the display unit 11.

The predetermined operation with respect to the eye-gaze input apparatus 1 is not particularly limited. In the present embodiment, however, an operation of pressing down a dedicated physical switch (not shown and, hereinafter, referred to as a "calibration switch") provided to the eye-gaze input apparatus 1 is employed.

This means that the calibration of the present embodiment starts with the operation of pressing down the calibration switch, and a shift amount Vo(xo,yo) from the reflection center Z toward the pupil center Mo detected at the time of calibration is set as the initial value of the reference shift amount.

The shift amount Vo(xo,yo) detected at the time when the calibration starts has been described as the initial value because the shift amount Vo(xo,yo) is updated sequentially, as will be described later. However, since it may be confusing to go into detail on the update of the reference shift amount Vo(xo,yo) at this point, the update of the reference shift amount Vo(xo,yo) is not taken into consideration below.

Here, the user's eye-gaze movement vector can be expressed as a vector proportional to a difference vector $\Delta V(\Delta x, \Delta y)$ of the shift amount $V(x,y)$ detected after the calibration from the reference shift amount Vo(xo,yo).

Since any unit is relevant to the unit of the eye-gaze movement vector, in the present embodiment, it is assumed that the proportional constant is 1, and the difference vector $\Delta V(\Delta x, \Delta y)$ per se is employed as the eye-gaze movement vector.

Thus, in the present embodiment, the eye-gaze detection is realized by detecting the eye-gaze movement vector $\Delta V(\Delta x, \Delta y)$.

When the calibration is performed, at the same time as the gaze position of the user gazing at the center position of the display unit 11 is set as the initial value of the reference shift amount Vo(xo,yo), the center position of the display unit 11 is set as the initial position of the mouse pointer. In this way, it becomes possible to easily calculate a moving amount of the mouse pointer from the initial position based on the eye-gaze movement vector $\Delta V(\Delta x, \Delta y)$. Thus, processing of moving the mouse pointer can be easily made possible in accordance with the moving amount of the mouse pointer from the initial position.

Incidentally, in a case in which the user closes his or her eyes or turns his or her eyes away from the display unit 11, it becomes impossible to detect the eye-gaze movement vector $\Delta V(\Delta x, \Delta y)$. In such a case, however, it suffices that the eye-gaze input apparatus 1 halts the processing of moving the mouse pointer and waits until the eye-gaze movement vector $\Delta V(\Delta x, \Delta y)$ is detected again.

When the eye-gaze input apparatus 1 detects the eye-gaze movement vector $\Delta V(\Delta x, \Delta y)$ again, if the user's posture has not been changed so much, the previous calibration is still valid. Therefore, it is possible to resume the processing of moving the mouse pointer following the user's gaze position.

There can naturally be a case in which the gaze position of the user does not coincide any more with the mouse pointer position if the user drastically moves his or her eye gaze or greatly changes his or her posture. Even in such a case, however, the eye-gaze input apparatus 1 can easily set the mouse pointer position to coincide with the gaze position of the user by performing the calibration again.

In the above, a description has been given of the method of eye-gaze detection based on the relative relationship in position between the pupil center M and the reflection center Z.

In the following, a description will be given of the functional configuration to implement the execution function of input processing in accordance with such a method of eye-gaze detection from among the functions of the eye-gaze input apparatus 1 shown in FIG. 1.

Figure 6:
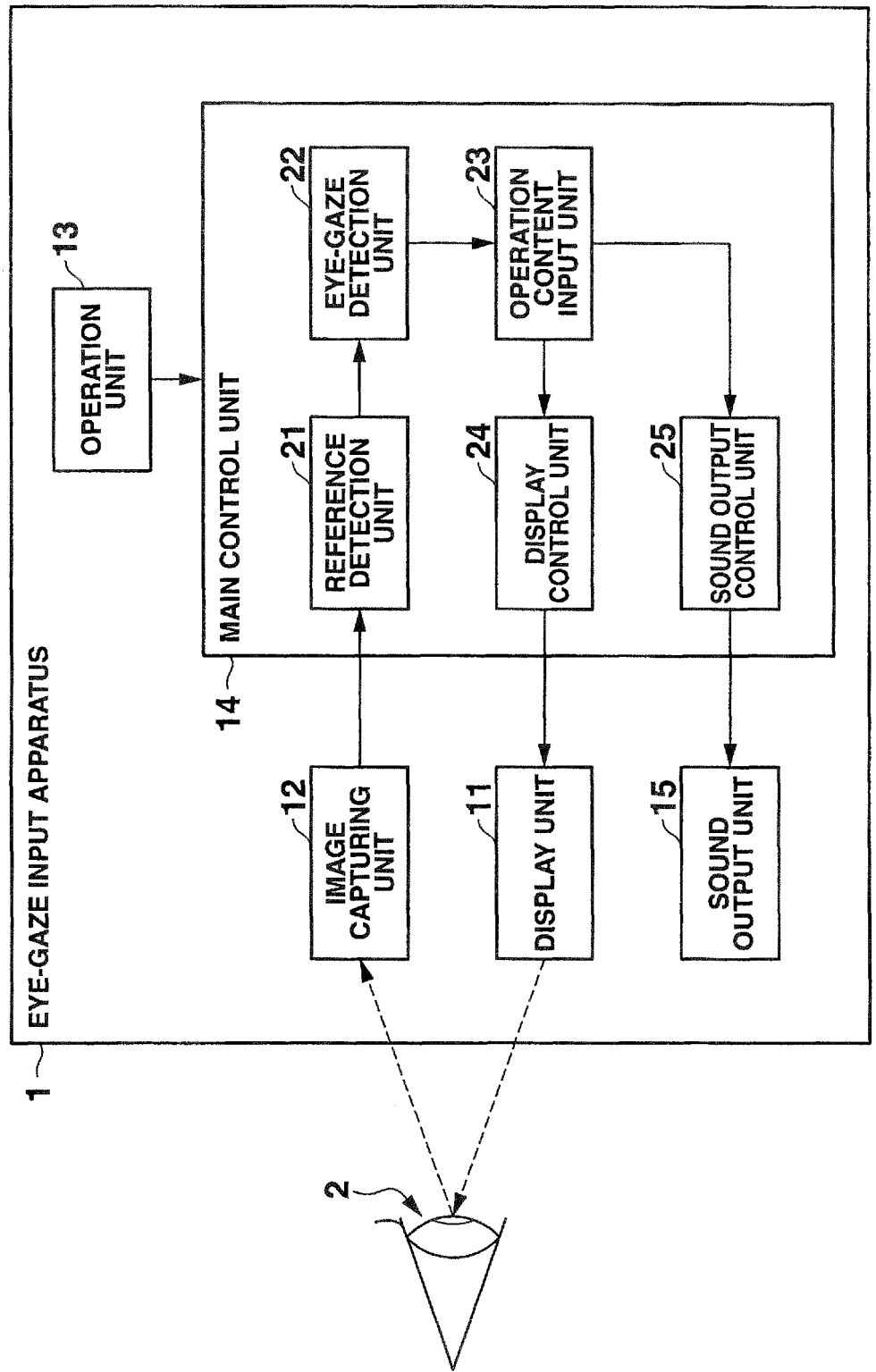
FIG. 6 is a functional block diagram showing a functional configuration of the eye-gaze input apparatus shown in FIG. 1.

FIG. 6 is a functional block diagram showing a functional configuration of the eye-gaze input apparatus 1 shown in FIG. 1.

In addition to the display unit 11 and the image capturing unit 12 described above, the eye-gaze input apparatus 1 is further provided with an operation unit 13, a main control unit 14, and a sound output unit 15.

The operation unit 13 is constituted by various physical switches such as the calibration switch described above.

As operation modes, the eye-gaze input apparatus 1 has a mode (hereinafter, referred to as an "eye-gaze mode") that operates to accept the mouse equivalent operation utilizing the eye-gaze movement, and a mode (hereinafter, referred to as a "normal mode") that operates to accept normal mouse operations in a conventionally existing fashion.

For this reason, the operation unit 13 includes a switch (hereinafter, referred to as an "eye-gaze mode switch") for issuing an instruction to select the eye-gaze mode, and a switch (hereinafter, referred to as a "normal mode switch") for issuing an instruction to select the normal mode, though not illustrated.

After the eye-gaze mode switch is pressed down, i.e., after the operation mode is switched to the eye-gaze mode, it is necessary that the above-described calibration be performed before the eye-gaze detection is carried out for the first time.

Therefore, each time the eye-gaze mode switch is pressed down, the calibration is also performed. This is equivalent to assigning both the instruction function of starting the calibration and the instruction function of selecting the eye-gaze mode to the eye-gaze mode switch. Therefore, the calibration switch is not necessarily a requisite constituent element of the operation unit 13.

From the viewpoint of usability, however, in order to make it easier for the user to understand the operation, it is preferable to assign the respective instruction functions of starting the calibration and of selecting the eye-gaze mode to different switches. Therefore, in the present embodiment, the calibration switch is provided separately from the eye-gaze mode switch.

In order to enable the normal mode operation, input devices such as a mouse are connectable with the eye-gaze input apparatus 1. However, since the eye-gaze input apparatus 1 can operate in the eye-gaze mode without input devices such as a mouse, input devices such as a mouse are not requisite constituent elements of the operation unit 13. Therefore, it is assumed that input devices such as a mouse are regarded as not being included in the constituent elements of the operation unit 13.

When the eye-gaze mode switch is pressed down and the eye-gaze input apparatus 1 operates in the eye-gaze mode, as shown in FIG. 6, a reference detection unit 21, an eye-gaze detection unit 22, an operation content input unit 23, a display control unit 24, and a sound output control unit 25 operate in the main control unit 14.

The reference detection unit 21 acquires data of a captured image as a result of capturing an image of the eye 2 of the user from the image capturing unit 12, and detects information (hereinafter, referred to as "reference information") to be used as the reference for the eye-gaze detection from the data of the captured image.

For example, the reference detection unit 21 identifies the pupil area 4 from the data of the captured image, and detects the coordinates of the pupil center M as the moving reference point, as one item of the reference information.

Further, for example, the reference detection unit 21 identifies the display unit reflection area 5 from the data of the captured image, and detects the coordinates of the reflection center Z as the unmoving reference point, as one item of the reference information.

More specifically, for example, the reference detection unit 21 identifies, as the display unit reflection area 5, a rectangular area having average luminance not below a predetermined threshold value and height and width satisfying a predetermined condition, from within a predetermined range centering on the pupil center M from the captured image.

As the predetermined condition, in the present embodiment, a condition is employed such that the height and width of the rectangular area fall within respective predetermined ranges as well as the ratio between the height and width of the rectangular area falls within a predetermined range.

Such a condition is applied for the purpose of excluding a possibility of misidentifying, as the display unit, an image reflection area 5 such as a bright rectangular reflection in the eye 2, more specifically, a reflection of a fluorescent lamp or a distant window, for example.

After that, from the display unit reflection area 5 thus identified, the reference detection unit 21 calculates the coordinates of the reflection center Z as described above.

Although the reference detection unit 21 may supply the coordinates of the pupil center M and the reflection center Z thus detected as the reference information to the eye-gaze detection unit 22, in the present embodiment, the reference detection unit 21 further acquires the shift amount V(x,y) as described above and supplies it as the reference information to the eye-gaze detection unit 22.

More specifically, for example, at the time of the calibration, the reference detection unit 21 detects the coordinates of the pupil center M and the reflection center Z, performs the initial setting of the reference shift amount Vo(xo,yo) described above, and supplies it as one item of the reference information to the eye-gaze detection unit 22.

After that, each time when the initial setting of the reference shift amount Vo(xo,yo) is performed, the reference detection unit 21 supplies it as one item of the reference information to the eye-gaze detection unit 22.

Furthermore, at a predetermined time interval, the reference detection unit 21 detects the coordinates of the pupil center M and the reflection center Z, acquires the above-described shift amount V(x,y) based on the detection result, and supplies it as one item of the reference information to the eye-gaze detection unit 22.

The eye-gaze detection unit 22 detects the gaze position of the eye 2 of the user based on these items of the reference information.

This means that, each time when the shift amount V(x,y) is supplied, the eye-gaze detection unit 22 calculates the eye-gaze movement vector $\Delta V(\Delta x,\Delta y)$ using the supplied shift amount V(x,y) and the reference shift amount Vo(xo,yo) stored at this time, and thereby detects the gaze position.

Based on the eye-gaze detection result, i.e., the eye-gaze movement vector $\Delta V(\Delta x,\Delta y)$, the eye-gaze detection unit 22 recognizes that one of the mouse equivalent operations has been performed, i.e., an operation equivalent to the instruction to move the mouse pointer has been performed, and notifies the operation content input unit 23 of the result of recognition.

This means that the eye-gaze detection unit 22 recognizes the mouse pointer movement amount (i.e., instruction to move the mouse pointer by the movement amount) corresponding to the eye-gaze movement vector $\Delta V(\Delta x,\Delta y)$, as follows:

When the horizontal element (in the X-axis direction) $\Delta x$ of the eye-gaze movement amount exceeds a predetermined threshold value, the eye-gaze detection unit 22 recognizes $\Delta x$ multiplied by a predetermined proportional constant as the horizontal element of the mouse pointer movement amount.

Similarly, when the vertical element (in the Y-axis direction) $\Delta y$ of the eye-gaze movement amount exceeds a predetermined threshold value, the eye-gaze detection unit 22 recognizes $\Delta y$ multiplied by a predetermined proportional constant as the vertical element of the mouse pointer movement amount.

The eye-gaze detection unit 22 supplies the above-described recognition result to the operation content input unit 23 as a content of the mouse equivalent operation.

The operation content input unit 23 inputs the content of the mouse equivalent operation supplied from the eye-gaze detection unit 22, and executes processing corresponding to the content.

For example, when the mouse pointer movement amount is supplied from the eye-gaze detection unit 22, the operation content input unit 23 inputs the mouse pointer movement amount, and executes processing of moving the mouse pointer by the input movement amount. This means that the operation content input unit 23 notifies the display control unit 24 of the mouse pointer movement amount.

The display control unit 24 executes a control of causing the display unit 11 to display a GUI (Graphical User Interface) screen including the mouse pointer.

This means that the display control unit 24 updates the position of the mouse pointer in the coordinate system of the display unit 11 based on the movement amount notified from the operation content input unit 23. In this manner, the mouse pointer actually moves in the GUI screen displayed on the display unit 11. More specifically, such a moving image is displayed on the display unit 11.

As the coordinate system of the display unit 11, it is assumed that a rightward X-axis and an upward Y-axis are employed.

In this manner, as described above, it becomes possible to realize the mirror image relationship such that the mouse pointer moves rightward in the coordinate system of the display unit 11 when the pupil center M moves leftward in the coordinate system of the captured image. A detailed description thereof will be given later with reference to FIGS. 11A and 11B.

After that, the eye-gaze detection unit 22 updates the reference shift amount Vo(xo,yo) in accordance with the mouse pointer movement.

This means that, when the mouse pointer has moved by a movement amount proportional to $\Delta x$ in a horizontal direction, the eye-gaze detection unit 22 updates the horizontal element xo of the reference shift amount Vo by adding thereto the eye-gaze movement amount $\Delta x$ (i.e., xo=x). Similarly, when the mouse pointer has moved by a movement amount proportional to $\Delta y$ in a vertical direction, the eye-gaze detection unit 22 updates the vertical element yo of the reference shift amount Vo by adding thereto the eye-gaze movement amount $\Delta y$ (i.e., yo=y).

Thus, the reference shift amount Vo(xo,yo) is updated, and the eye-gaze detection unit 22 stores the updated result. In this manner, it becomes possible to detect the subsequent eye-gaze movement from the new position of the mouse pointer, which coincides with the current gaze position.

It has been described that the mouse pointer position is updated only when $\Delta x$ or $\Delta y$ exceeds the threshold value. This is to evade an undesirable fluctuation of the mouse pointer due to a human nature of constant eye tremor.

The eye-gaze detection unit 22 can also recognize an operation equivalent to a click operation from among the mouse equivalent operations based on the eye state detected from the data of the captured image.

According to a known technique of detecting an eye blink, the eye-gaze detection unit 22 detects an eye blink motion from the data of the captured image. When 2 successive eye blink motions have been detected in a predetermined time interval, the eye-gaze detection unit 22 recognizes that an operation equivalent to the click operation has been performed, and supplies the recognition result to the operation content input unit 23.

When the recognition result is supplied, the operation content input unit 23 inputs an instruction content (e.g., an instruction to select an icon) associated with the click operation, and executes processing (e.g., processing of selecting an icon) in accordance with the input content.

Meanwhile, the mouse click operation includes a left click and a right click. In a case in which it is necessary to distinctly use the left click and the right click, for example, 2 successive left eye blink motions may be assigned to an operation equivalent to the left click, and 2 successive right eye blink motions may be assigned to an operation equivalent to the right click.

Furthermore, when a content of the mouse equivalent operation is input, the operation content input unit 23 supplies information indicative of an instruction to output a sound corresponding to the content, to the sound output control unit 25.

The sound output control unit 25 executes a control of causing the sound output unit 15 to output the sound specified by the information supplied from the operation content input unit 23, e.g., a click sound when an operation equivalent to the click operation is performed.

When the normal mode switch of the operation unit 13 is pressed down and the eye-gaze input apparatus 1 operates in the normal mode, the operation content input unit 23, the display control unit 24, and the sound output control unit 25 operate in the main control unit 14. However, since the normal mode operation is the same as conventionally existed operation, a description thereof is omitted here.

In the above, a description has been given of the functional configuration of the eye-gaze input apparatus 1 with reference to FIG. 6.

However, the above-described functional configuration of FIG. 6 is a mere example, and the eye-gaze input apparatus 1 may have any functional configuration as long as the apparatus as a whole can implement the various functions described above.

In the following, a description will be given of flow of processing (hereinafter, referred to as "information input processing") of inputting contents of the mouse equivalent operations or normal mouse operations from the processing carried out by the eye-gaze input apparatus 1 having the functional configuration shown in FIG. 6 with reference to FIGS. 7 to 14.

Figure 7:
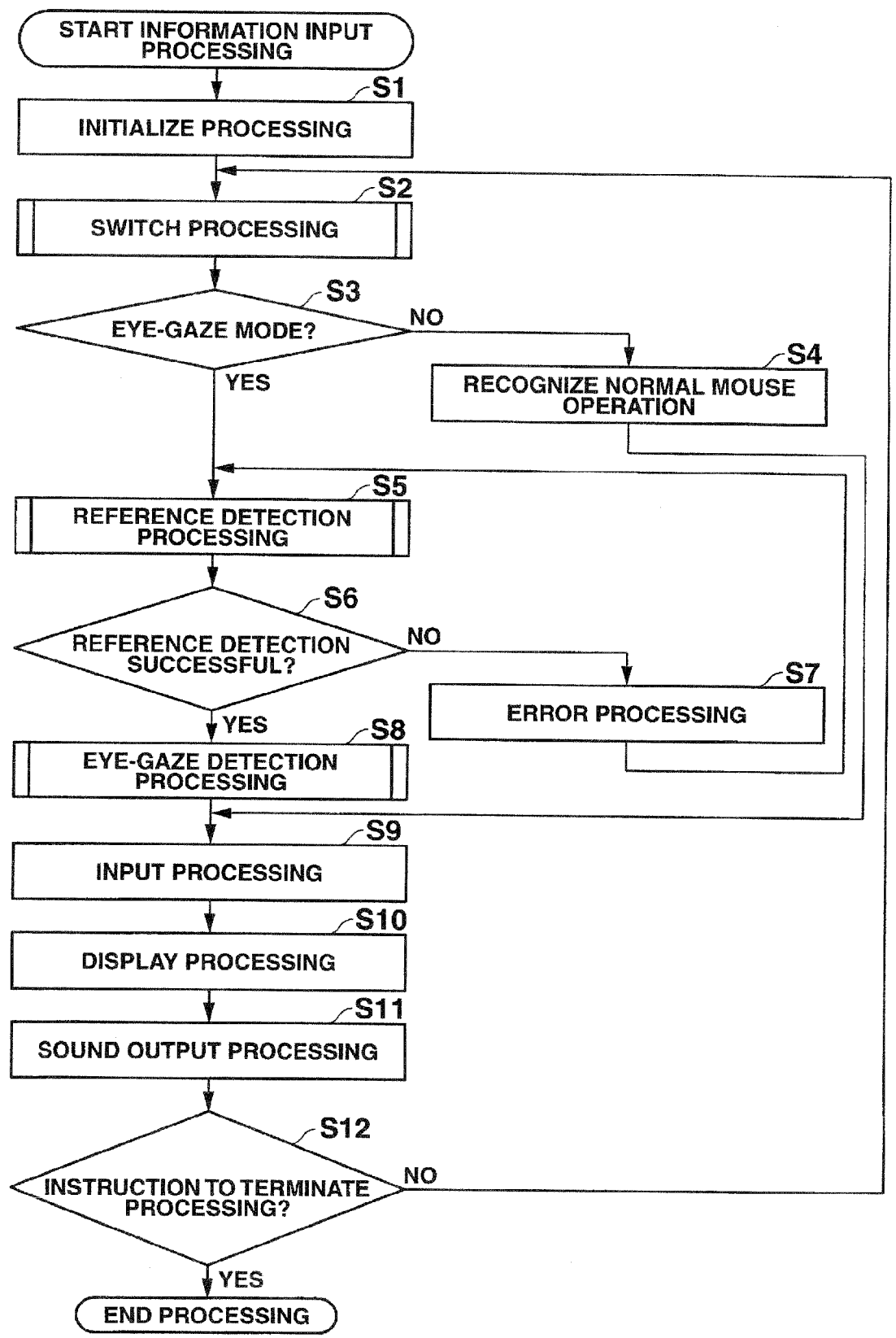
FIG. 7 is a flowchart showing one example of flow of information input processing carried out by the eye-gaze input apparatus shown in FIG. 6.

FIG. 7 is a flowchart showing one example of flow of the information input processing carried out by the eye-gaze input apparatus 1 shown in FIG. 6.

The information input processing starts, for example, when the power of the eye-gaze input apparatus 1 is turned on and a predetermined operation is performed by a user, then, the following processes of steps S1 to S12 are executed.

In step S1, the main control unit 14 executes initialize processing for initial setup of the entire eye-gaze input apparatus 1.

More specifically, for example, the main control unit 14 sets the normal mode as the initial setting of the operation mode, which will be set in the switch processing of step S2, which will be described later.

In the present embodiment, it is assumed that the eye-gaze mode is not allowed to be set as the initial setting of the operation mode. It is because the eye-gaze mode cannot start without carrying out the calibration, and therefore it requires the user to explicitly issue an instruction to start the eye-gaze mode.

In step S2, the main control unit 14 executes the switch processing.

The switch processing is intended to mean processing of setting such as selecting a predetermined option of a mode from among a plurality of options or selecting an initial state to a flag from among a plurality of states.

For example, in the switch processing of the present embodiment, a mode selected by the user from among the normal mode and the eye-gaze mode is set as the operation mode.

A further detailed description of the switch processing will be given later with reference to FIG. 8.

In step S3, the main control unit 14 determines whether or not the eye-gaze mode has been set.

If the normal mode has been set in the switch processing of step S2, a determination of NO is made in step S3, and control proceeds to step S4. In this case, since the user is required to perform the normal mouse operations, as described above, the operation content input unit 23, the display control unit 24, and the sound output control unit 25 operate in the main control unit 14 of FIG. 6.

In step S4, the operation content input unit 23 recognizes contents of a normal mouse operation.

After that, control proceeds to step S9. The processes of step S9 and thereafter will be described later.

On the other hand, if the eye-gaze mode has been set in the switch processing of step S2, a determination of YES is made in step S3, and control proceeds to step S5.

In step S5, the reference detection unit 21 executes reference detection processing.

The reference detection processing is intended to mean processing of detecting the reference information from the data of the captured image as a capturing result of an image of the eye 2, i.e., detecting the pupil center M (the moving reference point) and the reflection center Z (the unmoving reference point), calculating the shift amount V(x,y) based on the detection result, and initially setting the reference shift amount Vo(xo,yo), though main part thereof has already been described with reference to FIGS. 2 to 5. A detailed description thereof will be given later with reference to FIG. 9.

In step S6, the main control unit 14 determines whether or not the reflection center Z to be used as the unmoving reference point has been successfully detected in the reference detection processing of step S5.

If detection has failed to detect the reflection center Z in the reference detection processing of step S5, since it becomes impossible to execute the subsequent eye-gaze detection processing (the process of step S8, which will be described later), a determination of NO is made in step S6, and control proceeds to step S7.

In step S7, the main control unit 14 executes predetermined error processing.

After that, control goes back to the reference detection processing of step S5. This means that, until the reflection center Z is successfully detected, the loop processing from steps S5 to S7 is repeated.

If the reflection center Z is detected in the reference detection processing of step S5 at a number of times including the first time, a determination of YES is made in the subsequent step S6, and control proceeds to step S8.

In step S8, the eye-gaze detection unit 22 executes eye-gaze detection processing.

The eye-gaze detection processing is intended to mean processing such as one that acquires the eye-gaze movement vector ΔV(Δx,Δy) based on the reference shift amount Vo(xo, yo) and the shift amount V(x,y), which have been detected in the reference detection processing of step S5, thereby detects the gaze position, and recognizes the instruction to move the mouse pointer (determines the mouse pointer movement amount) based on the detection result. The eye-gaze detection processing also includes as a part thereof processing of detecting user's eye blinks and thereby recognizing an operation equivalent to the click operation. In short, the eye-gaze detection processing is processing that detects the gaze position and the eye blink and recognizes contents of the mouse equivalent operation based on the detection result or the like. A further detailed description of the eye-gaze detection processing will be described later with reference to FIG. 10.

In step S9, the operation content input unit 23 executes input processing that inputs a content of the mouse equivalent operation recognized in the eye-gaze detection processing of step S8, and executes processing corresponding to the input content as appropriate.

In step S10, the display control unit 24 executes display processing that causes the display unit 11 to display a GUI screen (such as a screen in which the mouse pointer moves) corresponding to the content of the mouse equivalent operation input in the process of step S9.

In step S11, the sound output control unit 25 executes sound output processing that causes the sound output unit 15 to output a sound such as a click sound, in accordance with the content of the mouse equivalent operation input in the process of step S9.

In step S12, the main control unit 14 determines whether or not it has been instructed to terminate the processing.

The instruction to terminate the processing is not particularly limited, and various instructions such as turning off the power of the eye-gaze input apparatus 1 may be employed as the instruction to terminate the processing.

If it has not yet been instructed to terminate the processing, a determination of NO is made in step S12, control goes back to step S2, and the processes thereafter are repeated.

This means that, until it is instructed to terminate the processing, the loop processing from steps S2 to S12 is repeatedly executed, each time when the user performs a mouse equivalent operation or a normal mouse operation, the content thereof is input, and processing corresponding to the input content is executed.

After that, when it is instructed to terminate the processing, a determination of YES is made in step S12, and the entire information input processing ends.

In the above, a description has been given of a flow of the information input processing with reference to FIG. 7.

In the following, a description will be given of a detailed flow of the switch processing of step S2 from the above-described information input processing.

Figure 8:
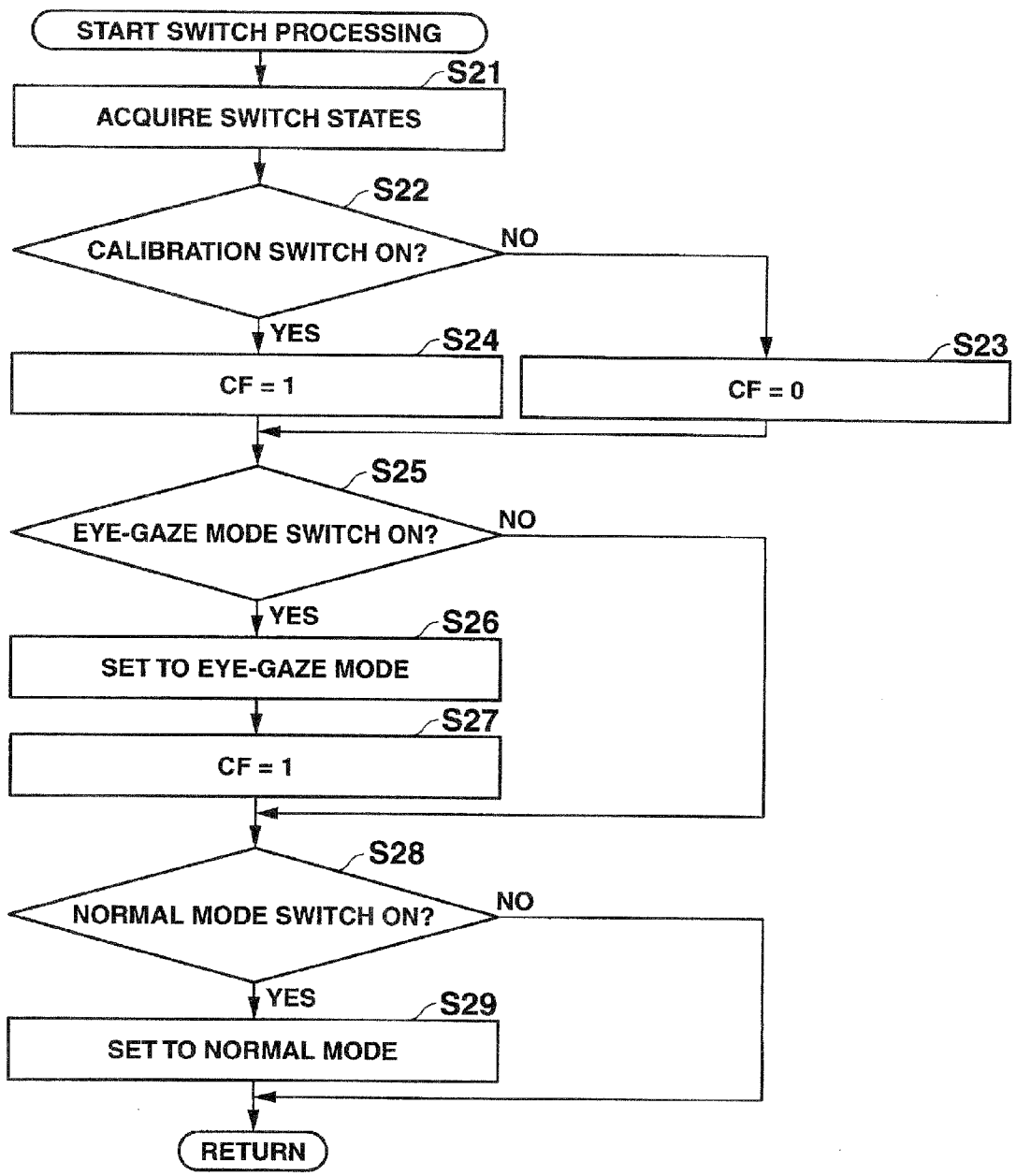
FIG. 8 is a flowchart showing one example of a detailed flow of switch processing from the information input processing shown in FIG. 7.

FIG. 8 is a flowchart showing a detailed flow of the switch processing.

In step S21, the main control unit 14 acquires information on the entire switch states from the operation unit 13.

The switch state is intended to mean ON state or OFF state. In the present embodiment, information regarding the switch states is acquired from the normal mode switch, the eye-gaze mode switch, and the calibration switch.

In step S22, the main control unit 14 determines whether or not the calibration switch is in ON state. If the calibration switch is in OFF state, a determination of NO is made in step S22, and control proceeds to step S23.

In step S23, the main control unit 14 sets CF flag to 0.

CF flag is a flag that indicates whether or not the calibration processing is required. This means that, when CF flag is set to 1, the calibration processing is required. On the other hand, as is after the process of the present step S23, when CF flag is set to 0, the calibration processing is not required.

After that, control proceeds to step S25. Processes of step S25 and thereafter will be described later.

On the other hand, if the calibration switch is in ON state, a determination of YES is made in step S22, and control proceeds to step S24.

In step S24, the main control unit 14 sets CF flag to 1. This indicates that the calibration processing is required.

In step S25, the main control unit 14 determines whether or not the eye-gaze mode switch is in ON state.

If the eye-gaze mode switch is in OFF state, a determination of NO is made in step S25, and control proceeds to step S28. Processes of step S28 and thereafter will be described later.

On the other hand, if the eye-gaze mode switch is in ON state, a determination of YES is made in step S25, and control proceeds to step S26.

In step S26, the main control unit 14 sets the eye-gaze mode as the operation mode of the eye-gaze input apparatus 1.

In step S27, the main control unit 14 sets CF flag to 1.

Here, even if CF flag has been set to 0 in the process of step S23, the press operation of the eye-gaze mode switch is assigned higher priority thereto, and thus CF flag is set to 1, which means that the calibration processing is required.

When the process of step S27 thus ends or NO is determined in step S25 (the eye-gaze mode switch is in OFF state), control proceeds to step S28.

In step S28, the main control unit 14 determines whether or not the normal mode switch is in ON state. If the normal mode switch is in OFF state, a determination of NO is made in step S28, and the switch processing ends.

On the other hand, if the normal mode switch is in ON state, a determination of YES is made in step S28, and control proceeds to step S29.

In step S29, the main control unit 14 sets the normal mode as the operation mode of the eye-gaze input apparatus 1. With this, the switch processing ends.

When the switch processing ends, i.e., the process of step S2 of FIG. 7 ends, control proceeds to step S3.

As described above, in the process of step S3, it is determined whether or not the operation mode of the eye-gaze input apparatus 1 is in the eye-gaze mode, and, if YES is determined, the reference detection processing of step S5 is to be executed.

Therefore, in the following, a description will be continued of a detailed flow of the reference detection processing of step S5.

Figure 9:
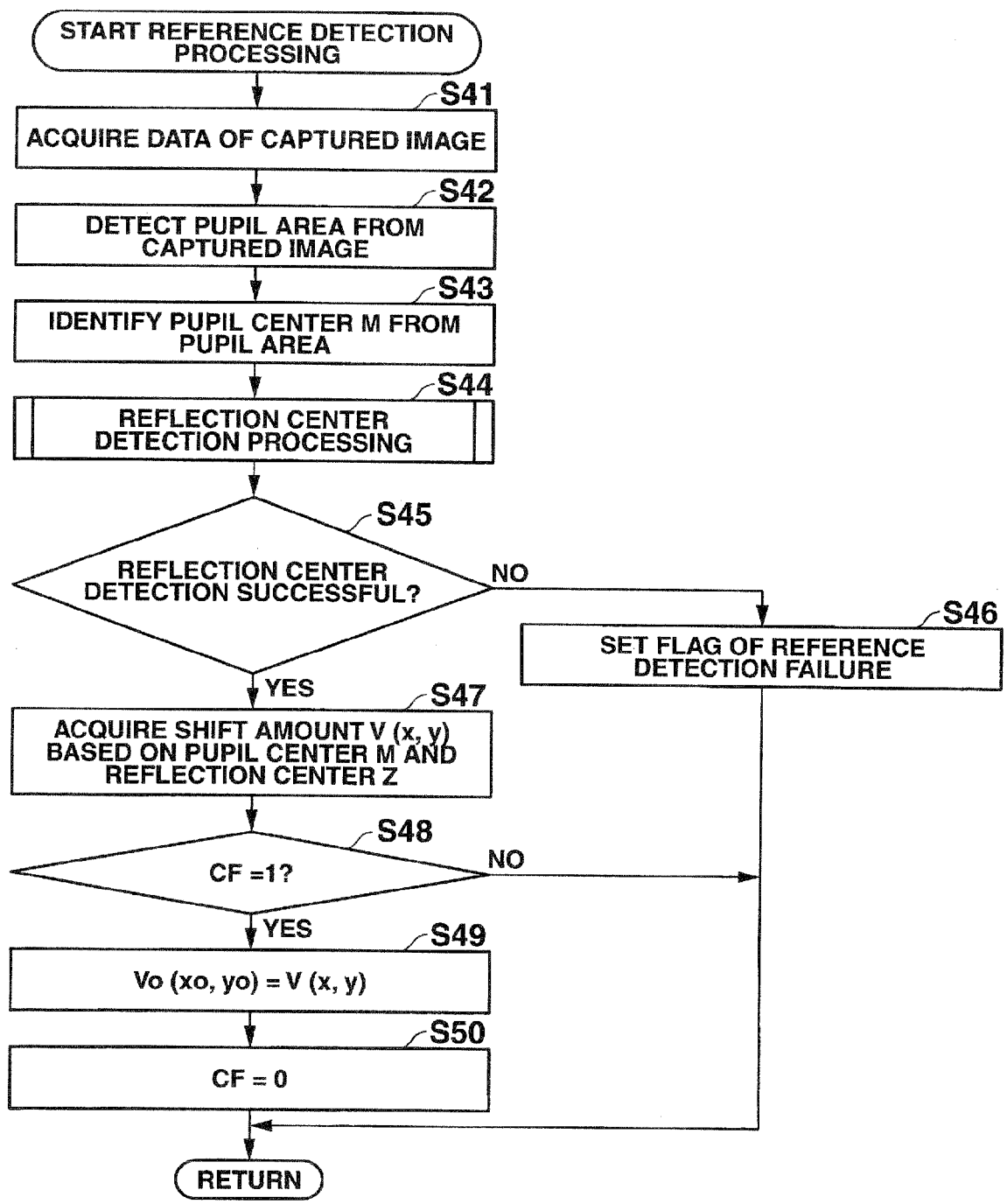
FIG. 9 is a flowchart showing one example of a detailed flow of reference detection processing from the information input processing shown in FIG. 7.

FIG. 9 is a flowchart showing a detailed flow of the reference detection processing.

In step S41, the reference detection unit 21 acquires from the image capturing unit 12 the data of the captured image as a capturing result of an image of the eye 2 of the user.

In step S42, the reference detection unit 21 detects the pupil area 4 from the data of the captured image acquired in the process of step S41.

In step S43, the reference detection unit 21 identifies the pupil center M as the moving reference point from the pupil area 4 detected in the process of step S42 as the gravity center thereof.

In step S44, the reference detection unit 21 executes reflection center detection processing.

The reflection center detection processing is intended to mean processing that detects the above-described reflection center Z as the unmoving reference point.

A further detailed description of the reflection center detection processing will be given with reference to FIGS. 12 to 14.

In step S45, the reference detection unit 21 determines whether or not the reflection center detection processing has succeeded.

If the reflection center detection processing has failed, a determination of NO is made in step S45, and control proceeds to step S46.

In step S46, the reference detection unit 21 sets a flag indicating a reference detection failure.

With this, the reference detection processing ends. This means that the process of step S5 of FIG. 7 ends, NO is determined in the process of the subsequent step S6, and the error processing of step S7 is to be executed.

On the other hand, if the reflection center detection processing has succeeded, a determination of YES is made in step S45, and control proceeds to step S47.

In step S47, the reference detection unit 21 acquires the shift amount V(x,y) based on the pupil center M identified in the process of step S43 and the reflection center Z identified in the reflection center detection processing of step S44, and supplies it to the eye-gaze detection unit 22.

In step S48, the reference detection unit 21 determines whether or not CF flag is set to 1.

If CF flag is 0, i.e., calibration is not required, a determination of NO is made in step S48, and the reference detection processing ends. This means that the process of step S5 of FIG. 7 ends, and control proceeds to step S6.

On the other hand, if CF flag is 1, i.e., calibration is needed, a determination of YES is made in step S48, and control proceeds to step S49.

In step S49, the reference detection unit 21 executes the calibration processing to initially set or update the reference shift amount Vo(xo,yo) to the shift amount V(x,y) acquired in the process of step S47 (Vo(xo,yo)=V(x,y)). At the same time, the reference detection unit 21 notifies the operation content input unit 23 of the event of the mouse pointer movement to the center position of the display unit 11, as the initial setting of the mouse pointer.

In step S50, the reference detection unit 21 sets CF flag to 0. This setting indicates that the calibration is not required for now, since the calibration has already been executed.

With this, the reference detection processing ends, i.e., the process of step S5 of FIG. 7 ends, and control proceeds to step S6.

In this case, YES is determined in step S6, and the eye-gaze detection processing of step S8 is to be executed.

Figure 10:
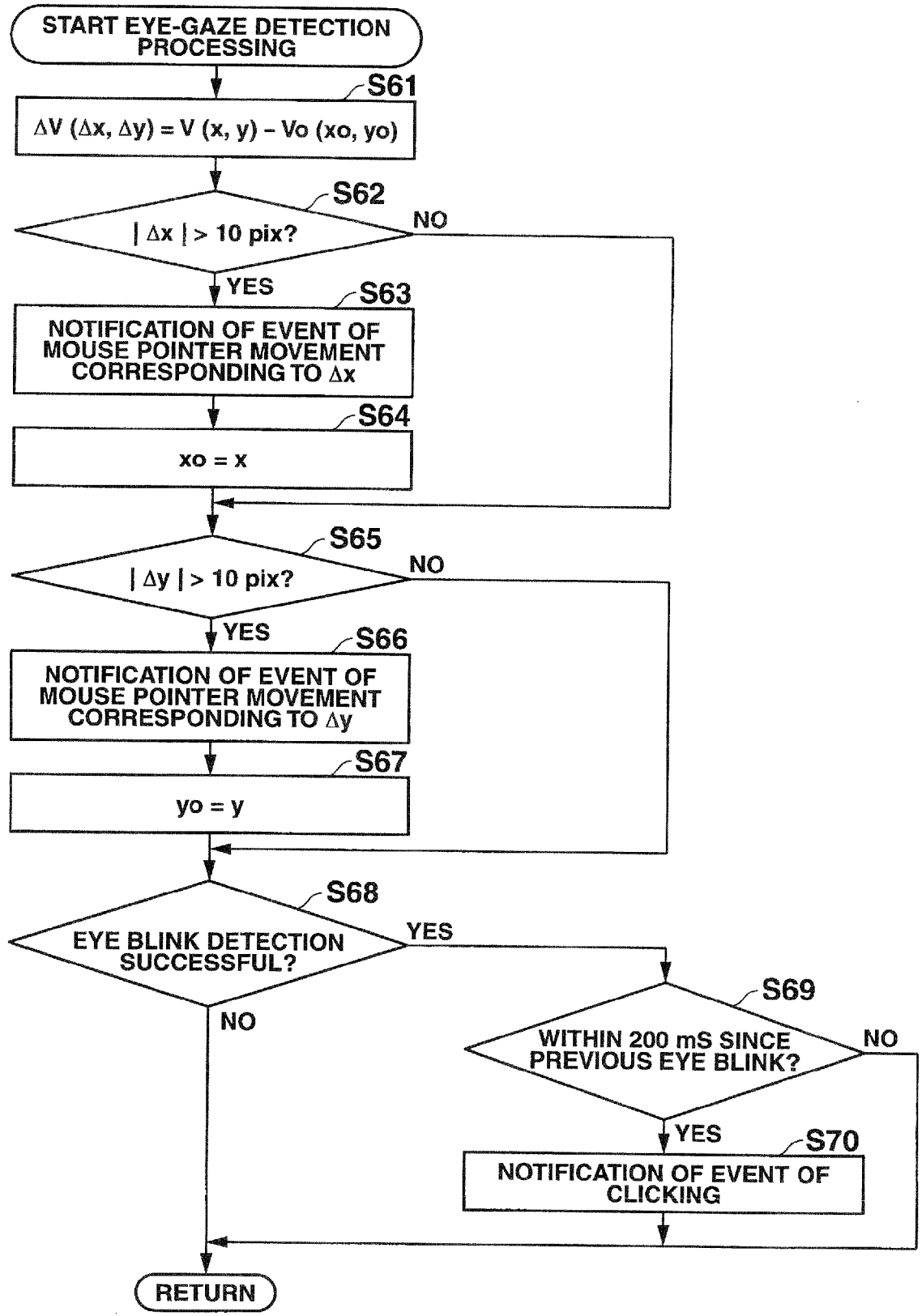
FIG. 10 is a flowchart showing one example of a detailed flow of eye-gaze detection processing from the information input processing shown in FIG. 7.

Therefore, in the following, a description will be continued of a detailed flow of the eye-gaze detection processing of step S8. FIG. 10 is a flowchart showing a detailed flow of the eye-gaze detection processing.

In step S61, the eye-gaze detection unit 22 calculates the eye-gaze movement vector $\Delta V(\Delta x, \Delta y)$ as a difference vector between the shift amount V(x,y) supplied from the reference detection unit 21 and the reference shift amount Vo(xo,yo) ($\Delta V(\Delta x, \Delta y) = V(x,y) - Vo(xo,yo)$).

In step S62, the eye-gaze detection unit 22 determines whether or not an absolute value of the horizontal element (in the X-axis direction) $\Delta x$ of the eye-gaze movement vector $\Delta V$ calculated in the process of step S61 exceeds 10 pixels ($|\Delta x| > 10$ pixels).

Here, it is assumed that a horizontal eye-gaze movement amount, which can be regarded with reliability that the user has moved his or her gaze position in order to instruct to horizontally move the mouse pointer, is set to at least 11 pixels in the pixels of the captured image.

Therefore, in a case in which the absolute value of the horizontal element (in the X-axis direction) $\Delta x$ of the eye-gaze movement vector $\Delta V$ does not exceed 10 pixels, it is determined that the user's eye-gaze may have been fluctuated due to eye tremor or the like without intention to move the mouse pointer, and therefore, any instruction to move the mouse pointer is not recognized.

In such a case, a determination of NO is made in step S62, and control proceeds to step S65 without executing the processes of steps S63 and S64, which are to be carried out to recognize the instruction to move the mouse pointer. Processes after step S65 will be described later.

On the other hand, in a case in which the absolute value of the horizontal element (in the X-axis direction) $\Delta x$ of the eye-gaze movement vector $\Delta V$ exceeds 10 pixels, it is recognized that the user moved his or her eye-gaze to instruct a horizontal movement of the mouse pointer. Thus, a determination of YES is made in step S62, and control proceeds to step S63.

In step S63, the eye-gaze detection unit 22 notifies the operation content input unit 23 of the event of the mouse pointer movement corresponding to the horizontal element (in the X-axis direction) $\Delta x$ of the eye-gaze movement vector $\Delta V$.

In step S64, the eye-gaze detection unit 22 updates the horizontal element (in the X-axis direction) xo of the reference shift amount Vo to the horizontal element (in the X-axis direction) x of the current shift amount V (xo=x) in accordance with the mouse pointer movement.

Consequently, in the process of step S61 of the eye-gaze detection processing of the next time, the eye-gaze movement vector $\Delta V(\Delta x, \Delta y)$ will be acquired referencing to the horizontal element (in the X-axis direction) x of the current shift amount V.

When the process of step S64 thus ends or NO is determined in the process of step S62, control proceeds to step S65.

In step S65, the eye-gaze detection unit 22 determines whether or not an absolute value of the vertical element (in the Y-axis direction) $\Delta y$ of the eye-gaze movement vector $\Delta V$ calculated in the process of step S61 exceeds 10 pixels ($|\Delta y| > 10$ pixels).

Here, it is assumed that a vertical eye-gaze movement amount, which can be regarded with reliability that the user has moved his or her gaze position in order to instruct to vertically move the mouse pointer, is set to at least 11 pixels in the pixels of the captured image.

Therefore, in a case in which the absolute value of the vertical element (in the Y-axis direction) $\Delta y$ of the eye-gaze movement vector $\Delta V$ does not exceed 10 pixels, it is determined that the user's eye-gaze may have been fluctuated due to eye tremor or the like without intention to move the mouse pointer, and any instruction to move the mouse pointer is not recognized.

In such a case, a determination of NO is made in step S65, and control proceeds to step S68 without executing the processes of steps S66 and S67, which are to be carried out to recognize the instruction to move the mouse pointer. Processes after step S68 will be described later.

On the other hand, in a case in which the absolute value of the vertical element (in the Y-axis direction) $\Delta y$ of the eye-gaze movement vector $\Delta V$ exceeds 10 pixels, it is recognized that the user moved his or her eye-gaze to instruct a vertical movement of the mouse pointer. Thus, a determination of YES is made in step S65, and control proceeds to step S66.

In step S66, the eye-gaze detection unit 22 notifies the operation content input unit 23 of the event of the mouse pointer movement corresponding to the vertical element (in the Y-axis direction) Δy of the eye-gaze movement vector ΔV.

In step S67, the eye-gaze detection unit 22 updates the vertical element (in the Y-axis direction) yo of the reference shift amount Vo to the vertical element (in the Y-axis direction) y of the current shift amount V (yo=y) in accordance with the mouse pointer movement.

Consequently, in the process of step S61 of the next time eye-gaze detection processing, the eye-gaze movement vector ΔV(Δx,Δy) will be acquired referencing to the vertical element (in the Y-axis direction) y of the current shift amount V.

When the process of step S67 thus ends or NO is determined in the process of step S65, control proceeds to step S68.

In step S68, the eye-gaze detection unit 22 determines whether or not a user's eye blink has been detected from the data of the captured image.

If no eye blinks have been detected, a determination of NO is made in step S68, the eye-gaze detection processing ends.

This means that the process of step S8 of FIG. 7 ends, and control proceeds to step S9
Here, if either of the processes of steps S63 and S66 has been executed, an instruction of the mouse pointer movement is input in the process of step S9, and the mouse pointer moves in the process of the subsequent step S10 (a GUI screen showing the movement is displayed).

On the other hand, if a user's eye blink has been detected, a determination of YES is made in step S68, and control proceeds to step S69.

In step S69, the eye-gaze detection unit 22 determines whether or not the eye blink currently detected has occurred within 200 mS since the previously detected eye blink.

If the time interval between the current and previous blinks exceeds 200 mS, it is recognized that the user didn't blink twice for the purpose of an operation equivalent to the click operation. Thus, a determination of NO is made in step S69, the eye-gaze detection processing ends.

This means that the process of step S8 of FIG. 7 ends, and control proceeds to step S9. Here, if either of the processes of steps S63 and S66 has been executed, an instruction of the mouse pointer movement is input in the process of step S9, and the mouse pointer moves in the process of the subsequent step S10 (a GUI screen showing the movement is displayed).

On the other hand, if the time interval between the current and previous blinks does not exceed 200 mS, it is recognized that the user has blinked twice for the purpose of an operation equivalent to the click operation. Thus, a determination of YES is made in step S69, and control proceeds to step S70.

In step S70, the eye-gaze detection unit 22 notifies the operation content input unit 23 of the event of the mouse click.

With this, the eye-gaze detection processing ends, i.e., the process of step S8 of FIG. 7 ends, and control proceeds to step S9.

Here, an instruction (such as of selecting an icon) associated with the detected click operation is input in the process of step S9, and processing according to the instruction is executed as appropriate.

In the above, a description has been given of flow of the eye-gaze detection processing of step S8 from the eye-gaze input processing of FIG. 7 with reference to FIG. 10.

The values such as 10 pixels employed in steps S62 and S65 and 200 mS employed in step S69 are mere examples, and freely changeable within a scope that does not deviate from the purpose of preventing misdetection.

In the following, a description will be given of the direction of the mouse pointer movement, which is determined by the eye-gaze detection processing, with reference to FIGS. 11A and 11B.

Figure 11A:
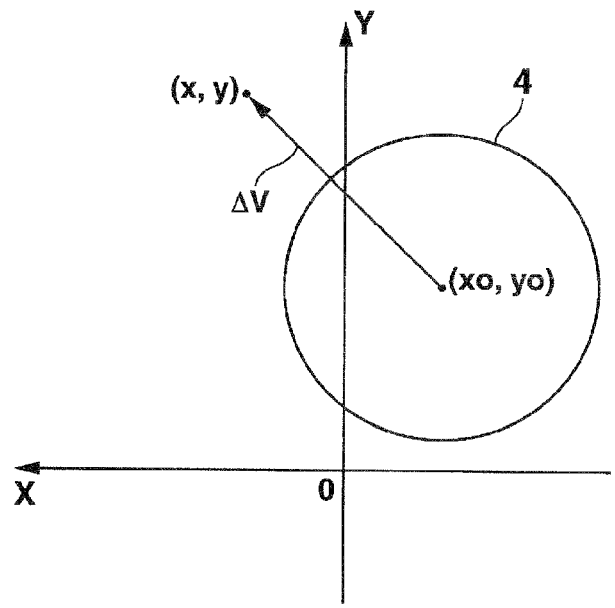
FIG. 11A is a diagram illustrating a direction of eye-gaze movement on the captured image, which is determined by the eye-gaze detection processing shown in FIG. 10.

FIG. 11A is a diagram illustrating a direction of eye-gaze movement on the captured image, which is determined by the eye-gaze detection processing. FIG. 11B is a diagram illustrating a direction of the mouse pointer movement on the display unit 11, which is determined by the eye-gaze detection processing.

In other words, FIG. 11A is a diagram illustrating a direction of the movement of the pupil center M in the coordinate system of the captured image having a new origin at the reflection center Z. By defining the reflection center Z as the origin, the coordinates of the pupil center M can be expressed by (x,y) so as to coincide with the shift amount V(x,y). Here, the eye-gaze movement is expressed by the vector ΔV, as described earlier.

Figure 11B:
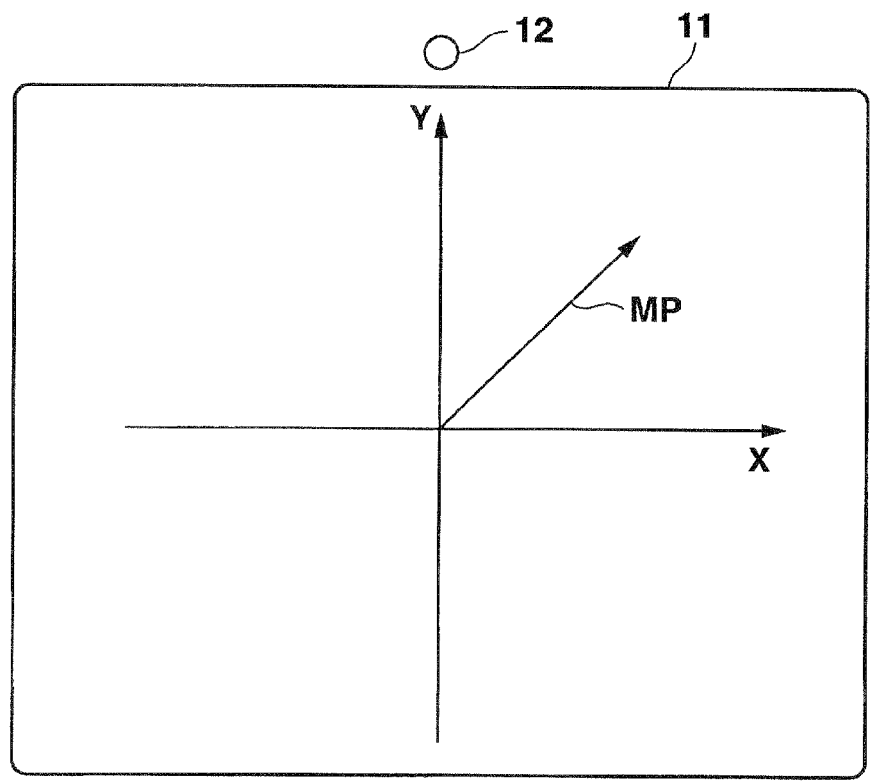
FIG. 11B is a diagram illustrating a direction of mouse pointer movement on the display unit 11, which is determined by the eye-gaze detection processing shown in FIG. 10.

Next, FIG. 11B also illustrates the direction of the mouse pointer movement, corresponding to the eye-gaze movement vector ΔV shown in FIG. 11A, in the coordinate system of the display unit 11 having the origin at the center thereof.

When the pupil center M moves in an upper left direction from the initial shift amount Vo(xo,yo) to the current shift amount V(x,y) as shown in FIG. 11A, the mouse pointer moves in an upper right direction as shown in FIG. 11B.

This is because the movement direction of the captured pupil center M shown in FIG. 11A is in a mirror image relationship with the moving direction of the mouse pointer, i.e., the gaze position seen from the user shown in FIG. 11B.

Changing the subject, in the following, respective descriptions will be given of three examples of the reflection center detection processing of step S44 from the reference detection processing of FIG. 9 (the process of step S5 of FIG. 7).

Figure 12:
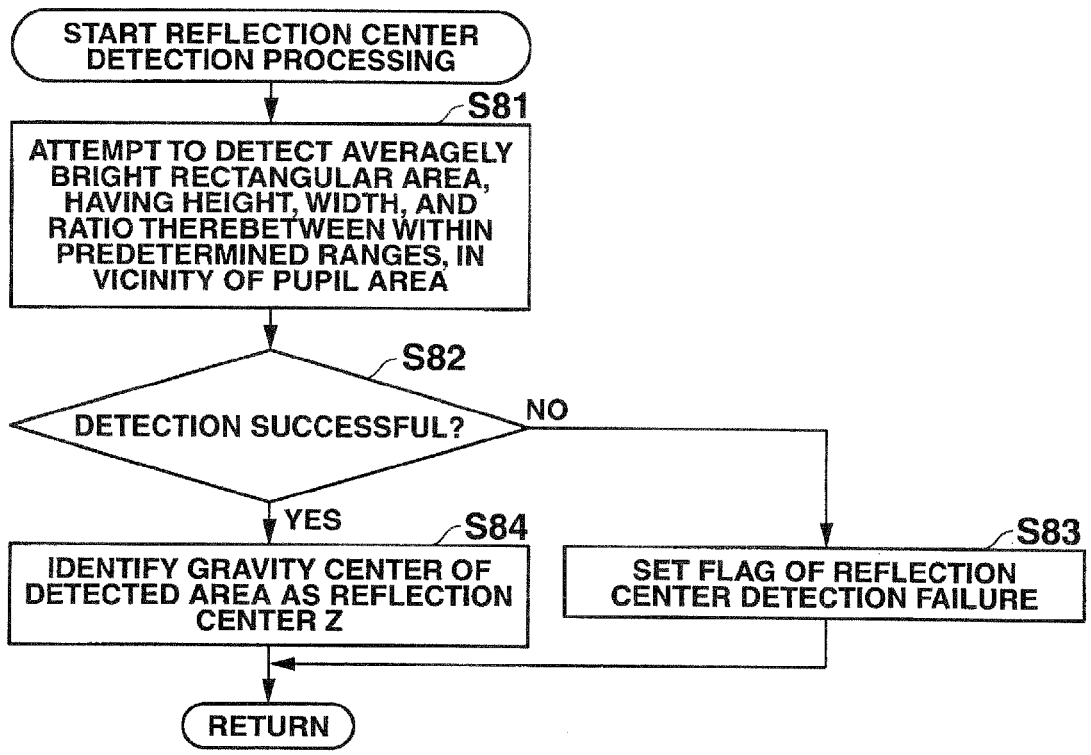
FIG. 12 is a flowchart showing one example of a detailed flow of reflection center detection processing from the reference detection processing shown in FIG. 9.

FIG. 12 is a flowchart showing one example of a detailed flow of the reflection center detection processing.

In step S81, the reference detection unit 21 attempts to detect an averagely bright rectangular area whose height, width, and ratio therebetween are within respective predetermined ranges, in the vicinity of the pupil area 4 in the captured image, more specifically, within a predetermined range centering on the pupil center M.

In step S82, the reference detection unit 21 determines whether or not an area has been detected by the attempt in the process of step S81.

If no area has been detected by the attempt in the process of step S81, a determination of NO is made in step S82, and control proceeds to step S83.

In step S83, the reference detection unit 21 sets a flag indicating that the reflection center has failed to be detected. With this, the reflection center detection processing ends. This means that the process of step S44 of FIG. 9 ends, and control proceeds to step S45. Here, NO is determined in the process of step S45, the reference detection failure flag is set, the reference detection processing ends, i.e., the process of step S5 of FIG. 7 ends, NO is determined in the process of step S6, and the error processing of step S7 is executed.

On the other hand, if an area has been detected by the attempt in the process of step S81, a determination of YES is made in step S82, and control proceeds to step S84.

In step S84, the reference detection unit 21, assumes the detected area as the display unit reflection area 5, and calculates the gravity center thereof as the coordinates of the reflection center Z.

With this, the reflection center detection processing ends. This means that the process of step S44 of FIG. 9 ends, and control proceeds to step S45. Here, YES is determined in the process of step S45, the shift amount V(x,y) and the like are calculated, and then, the reference detection processing ends. This means that the process of step S5 of FIG. 7 ends, YES is determined in the process of step S6, and then, the eye-gaze detection processing of step S8 is executed.

Figure 13:
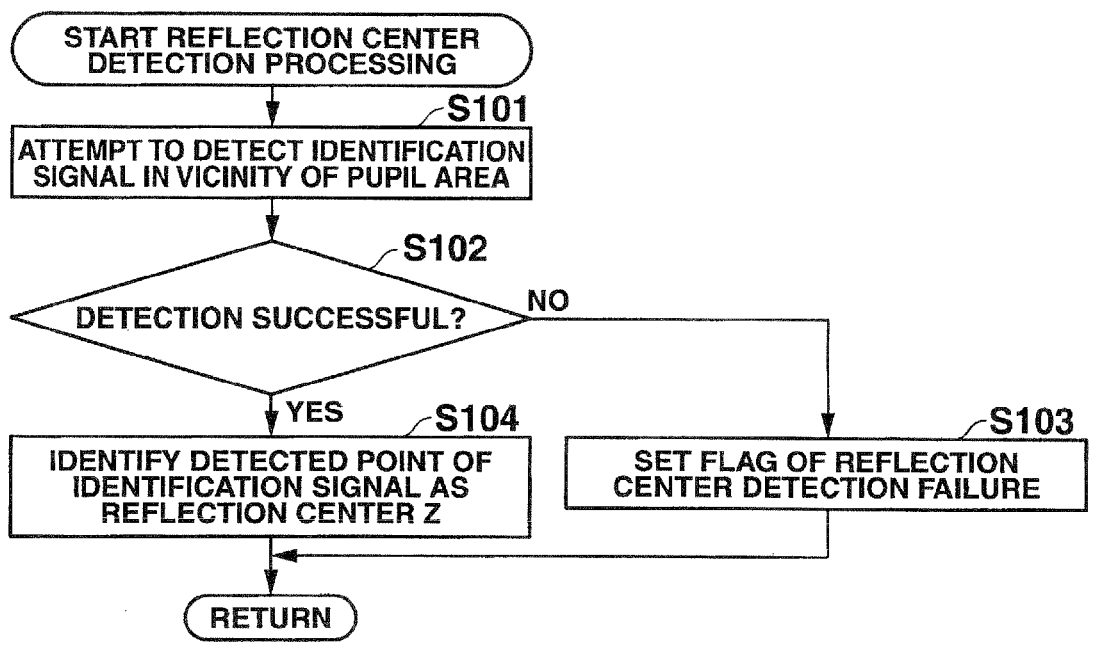
FIG. 13 is a flowchart showing another example, different from the example of FIG. 12, of a detailed flow of reflection center detection processing from the reference detection processing shown in FIG. 9.

FIG. 13 is a flowchart showing another example, different from the example of FIG. 12, of a detailed flow of the reflection center detection processing.

In step S101, the reference detection unit 21 attempts to detect an identification signal (an area in the captured image acquired as a result of capturing an image of a reflection of the identification signal in the eye 2 by the image capturing unit 12) sent from the center point of the display unit 11 in the vicinity of the pupil area 4 in the captured image, more specifically, within a predetermined range centering on the pupil center M by means of the known technology or the like.

This means that the point where the identification signal is detected by such an attempt is identified as the reflection center Z.

In this example, it is assumed that the display control unit 24 has a function of controlling the display unit 11 to emit a light modulated by the identification signal.

Since the processes of steps S102 to S104 and the flow thereof are basically the same as the steps S82 to S84 in the example of FIG. 12, a description thereof is omitted here.

Figure 14:
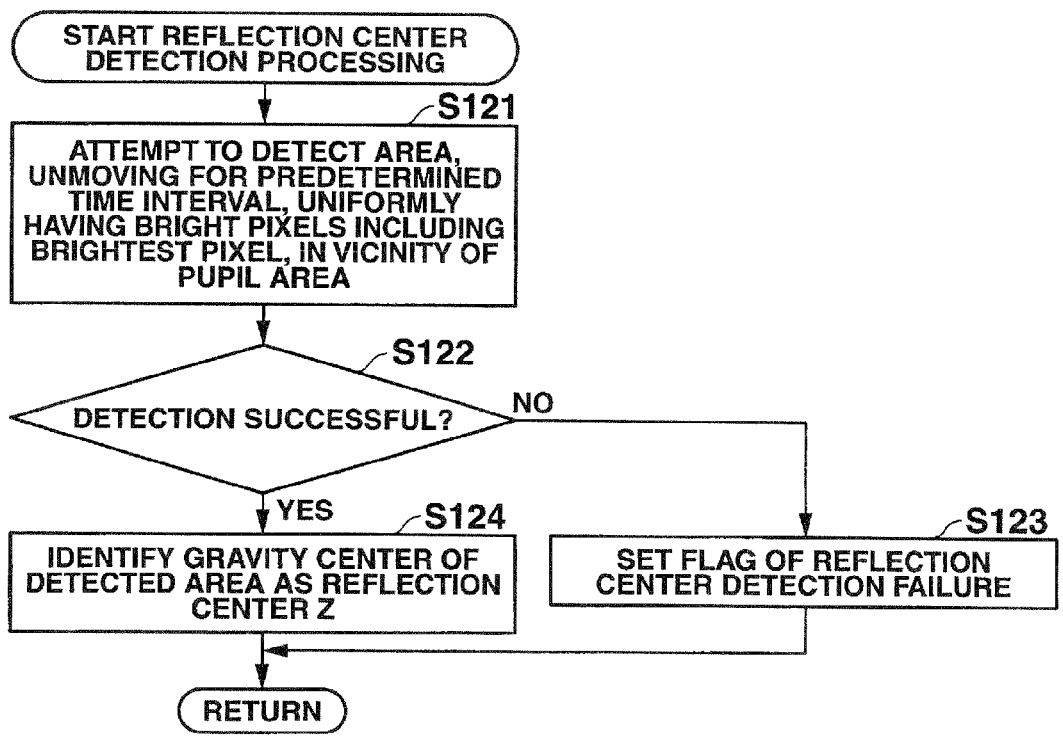
FIG. 14 is a flowchart showing another example, different from the examples of FIGS. 12 and 13, of a detailed flow of reflection center detection processing from the reference detection processing shown in FIG. 9.

FIG. 14 is a flowchart showing another example, different from the examples of FIGS. 12 and 13, of a detailed flow of the reflection center detection processing.

In step S121, the reference detection unit 21 attempts to detect an area, which is formed by continuous bright pixels including the brightest pixel, and has not been moved for a predetermined time interval, in the vicinity of the pupil area 4 in the captured image, more specifically, within a predetermined range centering on the pupil center M.

This means that the gravity center of the area detected by such an attempt is identified as the reflection center Z.

Although the predetermined time interval is not particularly limited, it is preferable to employ a time interval less than approximately 200 mS as the predetermined time interval. This is because the response of the eye-gaze detection may become slow if the time interval exceeds 200 mS.

Since the processes of steps S122 to S124 and the flow thereof are basically the same as the steps S82 to S84 in the example of FIG. 12, a description thereof is omitted here.

As described above, the eye-gaze input apparatus 1 according to the present embodiment is provided with a display unit 11, an image capturing unit 12, a reference detection unit 21, and an eye-gaze detection unit 22.

The display unit 11 has a display area of a predetermined shape and displays an image on the display area.

The image capturing unit 12 captures an image of the eye 2 of the user in which the display area is reflected, and thereby generates data of a captured image.

From the data of the captured image generated by the image capturing unit 12, the reference detection unit 21 detects a moving reference point that moves along with the user's eye-gaze movement and an unmoving reference point that can be assumed to remain approximately stationary regardless of the user's eye-gaze movement, and generates a vector drawn from the unmoving reference point to the moving reference point as a shift amount V(x,y).

The eye-gaze detection unit 22 detects a movement vector $\Delta V(\Delta x, \Delta y)$ as the user's eye-gaze movement amount based on a reference shift amount Vo(xo,yo) generated in the past and the shift amount V(x,y) currently generated.

In this manner, the eye-gaze input apparatus 1 can accept a mouse equivalent operation by means of the eye-gaze detection without constraining the user's head, the user can perform the mouse equivalent operation in a state in which his or her head and hands are free.

Among other user interfaces, a touch panel easily causes finger oil to adhere to a surface of the panel. As for a touch pad, many users do not like the sense of scratching with a finger. A remote controller requires laborious operations. On the other hand, the eye-gaze input apparatus 1 can realize a comfortable user interface eliminating all the defects of such user interfaces.

Furthermore, it is possible to stably realize a mouse equivalent operation, since the eye-gaze detection is steadily performed as long as the user is gazing at the display unit 11. Even if the user has turned his or her eyes away, the user can resume the mouse equivalent operation only by gazing again in the same posture as before.

It should be noted that the present invention is not limited to the embodiment described above, and any modifications and improvements thereto within a scope in which an object of the present invention can be realized, are included in the present invention.

For example, in the embodiment described above, the same calibration function has been assigned to the eye-gaze mode switch and the calibration switch. However, different kinds of calibration functions may be assigned respectively thereto.

When a user presses down the eye-gaze mode switch, since the mouse pointer has been moving in the normal mode, the user may well be gazing at the mouse pointer. Therefore, in this case, calibration can be carried out in such a manner as using the current position of the mouse pointer as the initial position.

On the other hand, when the user presses down the calibration switch, since the user may have a firm intention of recalibration, and it is possible that the mouse pointer fails to follow the user's eye-gaze. Therefore, in this case, as is in the embodiment described above, it is possible to carry out calibration in such a manner as using the center position of the display unit 11 as the initial position.

Furthermore, it has been described in the above-described embodiment that the information processing apparatus, which the present invention is applied to, is the eye-gaze input apparatus 1 configured by a digital photo frame.

However, the present invention is not limited to this and can be applied to any electronic device that is capable of the eye-gaze detection described above. The present invention is widely applicable, for example, to a personal computer, a portable navigation device, a portable game device, a cell phone, a portable information terminal, and the like.

The series of processes described above can be executed by hardware and also can be executed by software.

FIG. 15 is a block diagram showing a hardware configuration of the eye-gaze input apparatus 1 in a case in which the series of processes described above is executed by software.

The eye-gaze input apparatus 1 is provided with, as well as the display unit 11, the image capturing unit 12, the operation unit 13, and the sound output unit 15, described above, a CPU (Central Processing Unit) 101, a ROM (Read Only Memory) 102, a RAM (Random Access Memory) 103, a bus 104, an input/output interface 105, a storing unit 106, a communication unit 107, and a drive 108.

The CPU 101 executes various processes according to programs that are stored in the ROM 102. Alternatively, the CPU 101 executes various processes according to programs that are loaded from the storing unit 106 to the RAM 103.

The RAM 103 also stores data and the like necessary for the CPU 101 to execute the various processes as appropriate.

For example, the main control unit 14 can be configured as a combination of the CPU 101 as hardware, and programs stored in the ROM 102 and the like as software, from among the above-described constitutional elements shown in FIG. 6.

The CPU 101, the ROM 102, and the RAM 103 are connected with each other via the bus 104. The bus 104 is also connected with the input/output interface 105. The display unit 11, the image capturing unit 12, the operation unit 13, the sound output unit 15, the storing unit 106, the communication unit 107, and the drive 108 are connected with the input/output interface 105.

The storing unit 106 is configured by a hard disk and the like and temporarily stores data of captured images outputted from the image capturing unit 12. Also, the storing unit 106 stores various kinds of data necessary for various kinds of image processing, such as image data, values of various flags, threshold values, and the like.

The communication unit 107 controls communication with other devices via networks such as the Internet.

The removable media 111 such as a magnetic disk, an optical disk, a magneto-optical disk, or a semiconductor memory is mounted to the drive 108 as appropriate. Computer programs read via the drive 108 are installed in the storing unit 106 or the like as needed.

In a case in which the series of processes are to be executed by software, a program configuring the software is installed from a network or a storage medium into a computer or the like. The computer may be a computer embedded in dedicated hardware. Alternatively, the computer may be capable of executing various functions by installing various programs, i.e., a general-purpose personal computer, for example.

The storage medium containing the program can be constituted not only by the removable media 111 distributed separately from the device main body for supplying the program to a user, but also can be constituted by a storage medium or the like supplied to the user in a state incorporated in the device main body in advance. The removable media 111 is composed of a magnetic disk (including a floppy disk), an optical disk, a magnetic optical disk, or the like, for example. The optical disk is composed of a CD-ROM (Compact Disk-Read Only Memory), a DVD (Digital Versatile Disk), and the like. The magnetic optical disk is composed of an MD (Mini-Disk) or the like. The storage medium supplied to the user in the state incorporated in the device main body in advance includes the ROM 102 storing the program, a hard disk included in the storing unit 106, and the like, for example.

It should be noted that in the present specification the steps describing the program stored in the storage medium include not only the processing executed in a time series following this order, but also processing executed in parallel or individually, which is not necessarily executed in a time series.

What is claimed is:

1. An information processing apparatus including a display unit, the information processing apparatus comprising:
    a first image detection unit that detects, as a first image, an image indicative of a specific part of an eye in captured image data supplied from an image capturing unit connected therewith;
    a first detection unit that identifies a position of the first image in the captured image data;
    a second image detection unit that detects, as a second image, an image indicative of an object of a specific shape reflected by the eye from the captured image data;
    a second detection unit that identifies a position of the second image in the captured image data;
    an eye-gaze movement amount detection unit that detects a movement amount of a gaze of the eye captured by the image capturing unit based on a relationship between positions of the first image and the second image;
    a mouse pointer control unit that causes a mouse pointer displayed on the display unit to move within the display unit based on the movement amount of the gaze of the eye detected by the eye-gaze movement amount detection unit; and
    a reference shift amount setting unit that sets a reference shift amount that is used as a reference for a variation of the position of the first image and the position of the second image;
    wherein the reference shift amount setting unit updates the reference shift amount in accordance with movement of the mouse pointer.

2. The information processing apparatus as set forth in claim 1, wherein the second image detection unit detects, as the second image, an image whose horizontal and vertical sizes, and a ratio between the horizontal and vertical sizes, are within respective predetermined ranges.

3. The information processing apparatus as set forth in claim 1, wherein the display unit displays an image which is reflected by the eye and detected as the second image.

4. The information processing apparatus as set forth in claim 1, further comprising:
    a blink detection unit that detects an eye blink based on whether a predetermined operation has been done a predetermined number of times within a predetermined time period, and
    a notifying unit that causes generation of a notification signal indicative that a mouse click operation has been done if the eye blink has been detected.

5. A non-transitory computer readable storage medium having a program stored thereon for controlling a computer of an information processing apparatus which includes a display unit and which detects a movement amount of a gaze of an eye from captured image data supplied from an image capturing unit connected therewith, the program being executable to control the computer to function as units comprising:
    a first image detection unit that detects, as a first image, an image indicative of a specific part of an eye in captured image data supplied from the image capturing unit;
    a first detection unit that identifies a position of the first image in the captured image data;
    a second image detection unit that detects, as a second image, an image indicative of an object of a specific shape reflected by the eye from the captured image data;
    a second detection unit that identifies a position of the second image in the captured image data;
    an eye-gaze movement amount detection unit that detects a movement amount of a gaze of the eye captured by the image capturing unit based on a relationship between positions of the first image and the second image;
    a mouse pointer control unit that causes a mouse pointer displayed on the display unit to move within the display unit based on the movement amount of the gaze of the eye detected by the eye-gaze movement amount detection unit; and
    a reference shift amount setting unit that sets a reference shift amount that is used as a reference for a variation of the position of the first image and the position of the second image;
    wherein the reference shift amount setting unit updates the reference shift amount in accordance with movement of the mouse pointer.

6. An information processing method of an information processing apparatus including a display unit for detecting a movement amount of a gaze of an eye from captured image data supplied from an image capturing unit, the method comprising;
- detecting, as a first image, an image indicative of a specific part of an eye in captured image data supplied from the image capturing unit;
- identifying a position of the first image in the captured image data;
- detecting, as a second image, an image indicative of an object of a specific shape reflected by the eye from the captured image data;
- identifying a position of the second image in the captured image data;
- detecting a movement amount of a gaze of the eye captured by the image capturing unit based on a relationship between positions of the first image and the second image;
- controlling a mouse pointer control unit displayed on the display unit to move within the display unit based on the detected movement amount of the gaze of the eye; and
- setting a reference shift amount that is used as a reference for a variation of the position of the first image and the position of the second image;
- wherein the reference shift amount is updated in accordance with movement of the mouse pointer.

* * * * *